US007009059B2

(12) United States Patent
Wurziger et al.

(10) Patent No.: US 7,009,059 B2
(45) Date of Patent: Mar. 7, 2006

(54) METHOD FOR THE 1,3 DIPOLAR CYCLOADDITION OF ORGANIC COMPOUNDS IN A MICROREACTOR

(75) Inventors: Hanns Wurziger, Darmstadt (DE); Joeran Stoldt, Darmstadt (DE); Guido Pieper, Mannheim (DE); Norbert Schwesinger, Eching (DE)

(73) Assignee: Merck Patent GmbH, Darmstadt (DE)

( * ) Notice: Subject to any disclaimer, the term of this patent is extended or adjusted under 35 U.S.C. 154(b) by 298 days.

(21) Appl. No.: 10/239,559

(22) PCT Filed: Mar. 6, 2001

(86) PCT No.: PCT/EP01/02515

§ 371 (c)(1),
(2), (4) Date: Apr. 18, 2003

(87) PCT Pub. No.: WO01/74822

PCT Pub. Date: Oct. 11, 2001

(65) Prior Publication Data

US 2003/0158421 A1   Aug. 21, 2003

(30) Foreign Application Priority Data

Mar. 30, 2000   (DE) ................................. 100 15 520

(51) Int. Cl.
*C07D 498/04* (2006.01)
*C07B 37/10* (2006.01)
(52) U.S. Cl. ..................................................... 548/242
(58) Field of Classification Search ................. 548/242
See application file for complete search history.

(56) References Cited

U.S. PATENT DOCUMENTS 5,904,424 A   5/1999   Schwesinger et al.

FOREIGN PATENT DOCUMENTS

WO   WO 96/30113      10/1996
WO   WO-96/30113   *  10/1996

OTHER PUBLICATIONS

Shanley et al., Chemical Engineering, 104(3), 30-33, Mar. 1997.*
Lowe et al., Electrochemica Acta, 44, 3679-3689, 1999.*
Ehrfeld et al., DECHEMA Monographien, 132, 1-28, 1996.*
Bernard et al., Chemical Abstracts, 129:110475, 1998.*
Zech et al., Chemical Abstracts, 130:54018, 1998.*
DeWitt , Chemical Abstracts, 131:20631, 1999.*
Okamoto, Chemical Abstracts, 131:242763, 1999.*
Lee et al., Synthetic Communications, 26(17), 3201-3215, 1996.*
Lee, J.I. et al., "An efficient synthesis of benzopyrano-2-Isoxazloines", Synth. Commun., vol. 26, No. 17, 1996, pp. 3201-3215, XP001010027.
Search Report for App. No. PCT/EP01/02515, Jun. 28, 2001.

* cited by examiner

*Primary Examiner*—Fiona T. Powers
(74) *Attorney, Agent, or Firm*—Millen, White, Zelano & Branigan, P.C.

(57) ABSTRACT

The invention relates to a method for the 1,3 dipolar cycloaddition of organic compounds, characterized in that the reaction is carried out in a microreactor.

22 Claims, No Drawings

METHOD FOR THE 1,3 DIPOLAR CYCLOADDITION OF ORGANIC COMPOUNDS IN A MICROREACTOR

The present invention relates to a method for the 1,3-dipolar cycloaddition of organic compounds.

The 1,3-dipolar cycloaddition of organic compounds is a method which is carried out very frequently in the chemical industry and whose great importance is also reflected in numerous publications on this subject.

However, the performance of 1,3-dipolar cycloadditions of organic compounds on an industrial scale is associated with safety problems and risks. Firstly, use is frequently made of relatively large amounts of highly toxic chemical substances, which even alone represent a considerable risk to humans and the environment, and secondly 1,3-dipolar cycloadditions of organic compounds frequently proceed very highly exothermically, which means that there is an increased risk of explosion when these reactions are carried out on an industrial scale. The attainment of official approval in accordance with the German Federal Emissions Protection Act (BimschG) for the operation of plants for the 1,3-dipolar cycloaddition of organic compounds on an industrial scale is therefore associated with considerable effort.

The object of the present invention is therefore to provide a method for the 1,3-dipolar cycloaddition of organic compounds which avoids the above-mentioned disadvantages. The aim is, in particular, for it to be possible for this method to be carried out in a simple, reproducible manner with increased safety for humans and the environment and with good yields and for the reaction conditions to be readily controllable.

This object is achieved, surprisingly, by the method according to the invention for the 1,3-dipolar cycloaddition of organic compounds, in which at least one organic compound in liquid or dissolved form is mixed with at least one dipolarophile in liquid or dissolved form in at least one microreactor and reacted for a residence time, and the organic cycloaddition compound formed is, if desired, isolated from the reaction mixture.

Advantageous embodiments of the method according to the invention are described in the sub-claims.

In accordance with the invention, an organic compound or a mixture of at least two of these compounds can be employed in the claimed method. In a preferred embodiment, in each case only one organic compound is used.

For the puropses of the invention, at least one organic compound having 1,3-dipolar properties is reacted with at least one dipolarophile or the organic compound simultaneously contains at least one functional group having 1,3-dipolar properties and at least one functional group having dipolarophilic properties. The 1,3-dipolar and dipolarophilic functional groups may in each case be identical or different. Preferably, in each case only one 1,3-dipolar group and one dipolarophilic group are present. As a consequence, both intermolecular and intramolecular cycloadditions are covered.

The organic compounds can be employed as pure compounds or prepared in situ from suitable precursor compounds and scavenged directly by dipolarophiles with formation of the corresponding cycloaddition product(s). The organic compounds are preferably prepared in situ and scavenged directly by dipolarophiles.

For the purposes of the invention, a microreactor is a reactor having a volume of $\leq 1000\ \mu l$ in which the liquids and/or solutions are intimately mixed at least once. The volume of the reactor is preferably $\leq 100\ \mu l$, particularly preferably $\leq 50\ \mu l$.

The microreactor is preferably made from thin silicon structures connected to one another.

The microreactor is preferably a miniaturised flow reactor, particularly preferably a static micromixer. The microreactor is very particularly preferably a static micromixer as described in the patent application with the international publication number WO 96/30113, which is incorporated herein by way of reference and is regarded as part of the disclosure.

A microreactor of this type has small channels in which liquids and/or chemical compounds in the form of solutions are mixed with one another by means of the kinetic energy of the flowing liquids and/or solutions.

The channels of the microreactor preferably have a diameter of from 10 to 1000 $\mu m$, particularly preferably from 20 to 800 $\mu m$ and very particularly preferably from 30 to 400 $\mu m$.

The liquids and/or solutions are preferably pumped into the microreactor in such a way that they flow through the latter at a flow rate of from 0.01 $\mu l/min$ to 100 ml/min, particularly preferably from 1 $\mu l/min$ to 1 ml/min.

In accordance with the invention, the microreactor is preferably heatable.

In accordance with the invention, the microreactor is preferably connected via an outlet to at least one residence zone, preferably a capillary, particularly preferably a heatable capillary. After mixing in the microreactor, the liquids and/or solutions are fed into this residence zone or capillary in order to extend their residence time.

For the purposes of the invention, the residence time is the time between mixing of the starting materials and work-up of the resultant reaction solution for analysis or isolation of the desired product(s).

The residence time necessary in the method according to the invention depends on various parameters, such as, for example, the temperature or reactivity of the starting materials. It is possible for the person skilled in the art to match the residence time to these various parameters and thus to achieve an optimum course of the reaction.

The residence time of the reaction solution in the system used, comprising at least one microreactor and, if desired, a residence zone can be set through the choice of the flow rate of the liquids and/or solutions employed.

The reaction mixture is likewise preferably passed through two or more microreactors connected in series. This achieves an extension of the residence time, even at an increased flow rate, and the 1,3-dipolar cycloaddition components employed are reacted to such an extent that an optimum product yield of the desired cycloaddition product(s) is achieved.

In a further embodiment, the reaction mixture is passed through two or more microreactors arranged in parallel in order to increase the throughput.

In another preferred embodiment of the method according to the invention, the number and arrangement of the channels in one or more microreactors are varied in such a way that the residence time is extended, likewise resulting in an optimum yield of the desired cycloaddition product(s) at an increased flow rate.

The residence time of the reaction solution in the microreactor, where appropriate in the microreactor and the residence zone, is preferably $\leq 15$ hours, particularly preferably $\leq 3$ hours, very particularly preferably $\leq 1$ hour.

The method according to the invention can be carried out in a very broad temperature range, which is essentially restricted by the heat resistance of the materials employed for the construction of the microreactor, any residence zone and further constituents, such as, for example, connections and seals, and by the physical properties of the solutions and/or liquids employed. The method according to the invention is preferably carried out at a temperature of from −100 to +250° C., particularly preferably from −78 to +150° C. and very particularly preferably from 0 to +40° C.

The method according to the invention can be carried out either continuously or batchwise. It is preferably carried out continuously.

For carrying out the method according to the invention for the 1,3-dipolar cycloaddition of organic compounds, it is necessary for the cycloaddition to be carried out as far as possible in the homogeneous liquid phase containing no or only very small solid particles, since otherwise the channels present in the microreactors become blocked.

The course of the 1,3-dipolar cycloaddition reaction in the method according to the invention can be followed using various analytical methods known to the person skilled in the art and if necessary regulated. The course of the reaction is preferably followed by chromatography, particularly preferably by high-pressure liquid chromatography, and if necessary regulated. Control of the reaction is significantly improved in the method according to the invention compared with known methods.

After the reaction, the organic compounds formed are isolated if desired. The cycloaddition product(s) is (are) preferably isolated from the reaction mixture by extraction.

Organic compounds which can be employed in the method according to the invention are all 1,3-dipolar organic compounds which are known to the person skilled in the art and are suitable as substrate for 1,3-dipolar cycloadditions. The organic compounds are preferably selected from aliphatic, aromatic or heteroaromatic nitrile ylides, nitrileimines, nitrile oxides, diazoalkanes, azides, azomethine ylides, azomethinimines, nitrones, carbonyl ylides, carbonylimines or carbonyl oxides.

Aliphatic nitrile ylides, nitrileimines, nitrile oxides, diazoalkanes, azides, azomethine ylides, azomethinimines, nitrones, carbonyl ylides, carbonylimines or carbonyl oxides which can be employed are all aliphatic compounds from the above-mentioned classes of substance which are known to the person skilled in the art and are suitable as substrate for 1,3-dipolar cycloadditions. Straight-chain, branched, cyclic, saturated and unsaturated compounds are also included.

Aromatic nitrile ylides, nitrileimines, nitrile oxides, diazoalkanes, azides, azomethine ylides, azomethinimines, nitrones, carbonyl ylides, carbonylimines or carbonyl oxides which can be employed are all aromatic compounds from the above-mentioned classes of substance which are known to the person skilled in the art and are suitable as substrate for 1,3-dipolar cycloadditions. The invention thus covers compounds and/or derivatives which have a monocyclic and/or polycyclic homoaromatic basic structure or a corresponding moiety, for example in the form of substituents.

Heteroaromatic nitrile ylides, nitrileimines, nitrile oxides, diazoalkanes, azides, azomethine ylides, azomethinimines, nitrones, carbonyl ylides, carbonylimines or carbonyl oxides which can be employed are all heteroaromatic compounds from the above-mentioned classes of substance which are known to the person skilled in the art and are suitable as substrate for 1,3-dipolar cycloadditions and contain at least one heteroatom. Heteroaromatic compounds for the purposes of the invention include heteroaromatic compounds and/or derivatives thereof which contain at least one monocyclic and/or polycyclic heteroaromatic basic structure or a corresponding moiety, for example in the form of substituents. Heteroaromatic basic structures or moieties particularly preferably include at least one oxygen, nitrogen and/or sulfur atom.

Dipolarophiles which can be employed in the method according to the invention are all dipolarophiles which are known to the person skilled in the art and are suitable for 1,3-dipolar cycloadditions, or a mixture of at least two dipolarophiles. Preferably, in each case only one compound is used as dipolarophile in the method according to the invention.

In a further preferred embodiment, the dipolarophile used is at least one compound selected from olefins, acetylenes, aldehydes, ketones, imines, nitrites, furans, thiophenes or mixtures of these dipolarophiles.

For the purposes of the invention, all dipolarophilic functional groups known to the person skilled in the art which react directly in 1,3-dipolar cycloadditions may be present in the various 1,3-dipolar organic compounds mentioned above. These compounds react in intramolecular cycloadditions if this is sterically possible. It is possible here for only one 1,3-dipolar functional group or a combination of at least two 1,3-dipolar functional groups and only one dipolarophilic group or a combination of at least two dipolarophilic groups, which are in each case identical or different, to be present in the organic compound in question. Preferably, only one 1,3-dipolar functional group and only one dipolarophilic functional group are present.

The molar ratio between the organic compound and the dipolarophile employed in the method according to the invention is dependent on the reactivity of the organic compounds and dipolarophiles employed. The molar ratio between the organic compound and the dipolarophile is preferably equimolar. In a further preferred embodiment, the dipolarophile is used in a 1.3-fold to 2-fold molar excess, particularly preferably in a 1.4-fold to 1.9-fold excess, very particularly preferably in a 1.5-fold to 1.8-fold excess, based on the organic compound.

The selectivity of the reaction itself depends on a number of further parameters in addition to the concentration of the reagents employed, such as, for example, the temperature, the type of dipolarophile used or the residence time. It is possible for the person skilled in the art to match the various parameters to the particular 1,3-dipolar cycloaddition in such a way that the desired cycloaddition product(s) is (are) obtained.

It is essential for the method according to the invention that the organic compounds and dipolarophiles employed are either themselves liquid or are in dissolved form. If these compounds are not already themselves in liquid form, they therefore have to be dissolved in a suitable solvent before the method according to the invention is carried out. The solvents employed are preferably water, ethers, particularly preferably diethyl ether, methyl tert-butyl ether, tetrahydrofuran or dioxane, aromatic solvents, particularly preferably toluene, xylenes, ligroin or phenyl ether, halogenated solvents, particularly preferably dichloromethane, chloroform, 1,2-dichloroethane or 1,1,2,2-tetrachloroethane, or mixtures thereof.

In the method according to the invention, the risk to humans and the environment caused by escaping chemicals is considerably reduced and thus results in increased safety on handling of hazardous substances. The 1,3-dipolar cycloaddition of organic compounds by the method according to the invention furthermore enables better control of the reaction conditions, such as, for example, reaction duration and reaction temperature, than is possible in the conventional methods. Furthermore, the risk of explosions in highly exothermic cycloadditions is significantly reduced on use of the method according to the invention. The temperature can be selected and kept constant individually in each volume unit of the system. The course of the 1,3-dipolar cycloaddition reaction can be regulated very quickly and precisely in the method according to the invention. The cycloaddition products can thus be obtained in very good and reproducible yields.

It is also particularly advantageous that the method according to the invention can be carried out continuously. It is thus faster and less expensive compared with conventional methods, and it is possible to prepare any desired amounts of the cycloaddition products without major measurement and regulation complexity.

The invention is explained below with reference to an example. This example serves merely to explain the invention and does not restrict the general inventive idea.

EXAMPLE

Oxidation of 5-bromo-2-allyloxybenzaldoxime to 5-bromo-2-allyloxybenzonitrile Oxide and 1,3-dipolar cycloaddition to 8-bromo-3α,4-dihydro-3H-[1]-benzopyrano[4,3-c]-2-isoxazole The oxidation of 5-bromo-2-allyloxybenzaldoxime using sodium hypochlorite solution to give 5-bromo-2-allyloxybenzonitrile oxide and the subsequent 1,3-dipolar cycloaddition were carried out in a static micromixer (Technical University of Ilmenau, Faculty of Machine Construction, Dr. Norbert Schwesinger, Postfach 100565, D-98684 Ilmenau) having a physical size of 40 mm×25 mm×1 mm with a total of 11 mixing stages each with a volume of 0.125 µl. The total pressure loss was about 1000 Pa.

The static micromixer was connected via an outlet and an Omnifit medium-pressure HPLC connector (Omnifit, Great Britain) to a Teflon capillary having an internal diameter of 0.49 mm and a length of 0.5 m. The reaction was carried out at room temperature, 10° C. or 0° C. In the case of the two latter temperatures, the temperature of the static micromixer and the Teflon capillary was regulated in an ethanol-filled double-wall vessel thermostatted to 10° C. or 0° C.

A 2 ml disposable syringe was filled with part of a solution of 0.5 g (2 mmol) of 5-bromo-2-allyloxybenzaldoxime and 10 ml of dichloromethane, and a further 2 ml syringe was filled with an approximately 10% aqueous sodium hypochlorite solution. The contents of the two syringes were subsequently transferred into the static micromixer using a metering pump (Harvard Apparatus Inc., Pump 22, South Natick, Mass., USA). Before the reaction was carried out, the experimental arrangement was calibrated with respect to the dependence of the residence time on the pump flow rate. The pump rate was set in such a way that residence times of 5, 2.5 and 1.25 minutes were achieved. The reaction was monitored with the aid of a Merck Hitachi LaChrom HPLC instrument. The ratios of starting material to product were also determined by HPLC on the above instrument.

What is claimed is:

1. A method for the 1,3-dipolar cycloaddition of an organic compound, comprising mixing at least one organic compound in liquid or dissolved form with at least one dipolarophile in liquid or dissolved form in at least one static micromixer connected via an outlet to a capillary, and reacting for a residence time wherein the reaction mixture flows through the microreactor at a flow rate of 0.01 –100 ml/min, and optionally isolating the formed organic cycloaddition product from the reaction mixture.

2. A method according to claim 1, wherein the volume of the microreactor is $\leq 100$ µl.

3. A method according to claim 1, wherein the microreactor is heatable.

4. A method according to claim 1, wherein the microreactor has channels having a diameter of 10–1000 µm.

5. A method according to claim 1, wherein the reaction mixture flows through the microreactor at a flow rate of 1 µl/min–1 ml/min.

6. A method according to claim 1, wherein the residence time of the compounds employed in the microreactor, or in the microreactor and the capillaries, is $\leq 15$ hours.

7. A method according to claim 1, wherein the method is carried out at $-100-+250°$ C.

8. A method according to claim 1, wherein the reaction is followed by chromatography.

9. A method according to claim 1, wherein the organic compound is an aliphatic, an aromatic or a heteroaromatic nitrile ylide, a nitrileimine, a nitrile oxide, a diazoalkane, an azide, an azomethine ylide, an azomethinimine, a nitrone, a carbonyl ylide, a carbonylimine or a carbonyl oxide.

10. A method according to claim 1, wherein the dipolarophile is at least one compound of an olefin, an acetylene, an aldehyde, a ketone, an imine, a nitrile, a furan, a thiophene or a mixture thereof.

11. A method according to claim 1, wherein the molar ratio between the organic compound and the dipolarophile is equimolar, based on the organic compound.

12. A method according to claim 1, wherein the capillary is heatable.

13. A method according to claim 1, wherein the volume of the microreactor is $\leq 50$ µl.

14. A method according to claim 1, wherein the microreactor has channels having a diameter of 20 –8000 µm.

15. A method according to claim 1, wherein the residence time of the compounds employed in the microreactor, or in the microreactor and the capillaries, is $\leq 3$ hour.

16. A method according to claim 1, wherein the method is carried out at $-78°-150°$ C.

17. A method according to claim 1, wherein the method is carried out at 0–40° C.

18. A method according to claim 1, wherein the reaction is followed by high-pressure liquid chromatography.

19. A method according to claim 1, wherein the dipolarophile is used in a 1.3-fold–2-fold molar excess, based on the organic compound.

20. A method according to claim 1, wherein the dipolarophile is used in a 1.4-fold–1.9-fold molar excess, based on the organic compound.

21. A method according to claim 1, wherein the cycloaddition reaction is conducted in a homogeneous liquid phase.

22. A method according to claim 21, wherein the homogenous liquid phase comprises no or only very small solid particles.

* * * * *

UNITED STATES PATENT AND TRADEMARK OFFICE
CERTIFICATE OF CORRECTION

PATENT NO.        : 7,009,059 B2
APPLICATION NO. : 10/239559
DATED             : March 7, 2006
INVENTOR(S)       : Hanns Wurziger It is certified that error appears in the above-identified patent and that said Letters Patent is hereby corrected as shown below:

On Front Page, Title reads "Method For The 1,3 Dipolar" should read -- Method For The 1,3-Dipolar--
On Front Page, PCT Date reads "Apr. 18, 2003" should read -- Sep. 24, 2002 --
Column 6, row 44 reads "3 hour" should read -- 3 hours --
Column 6, row 52 reads "wherein the dipolar-phile" should read -- wherein the dipolarophile --
Column 6, row 55 reads "wherein the dipolar-phile" should read -- wherein the dipolarophile --
Column 6, row 59 reads "homogeneous" should read -- homogenous --

Signed and Sealed this

Fifteenth Day of May, 2007

JON W. DUDAS
*Director of the United States Patent and Trademark Office*